(12) United States Patent
Carlucci et al.

(10) Patent No.: US 8,466,336 B2
(45) Date of Patent: *Jun. 18, 2013

(54) THIN ABSORBENT CORE SUBSTANTIALLY FREE OF CELLULOSE FIBERS

(75) Inventors: Giovanni Carlucci, Chieti (IT); Maurizio Tamburro, S. Giovanni Teatino (IT); Alessandro Gagliardini, Villa Vomano (IT); Evelina Toro, Chieti (IT); Pancrazio Veronese, Pescara (IT)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/588,614

(22) Filed: Aug. 17, 2012

(65) Prior Publication Data

US 2012/0316531 A1  Dec. 13, 2012

Related U.S. Application Data

(63) Continuation of application No. 12/180,751, filed on Jul. 28, 2008, now Pat. No. 8,263,820.

(30) Foreign Application Priority Data

Aug. 10, 2007  (EP) ..................................... 07015805

(51) Int. Cl.
*A61F 13/15* (2006.01)

(52) U.S. Cl.
USPC ............ 604/370; 604/367; 604/374; 604/378

(58) Field of Classification Search
USPC .......................... 604/366, 369, 370, 374–378
See application file for complete search history.

(56) References Cited

U.S. PATENT DOCUMENTS

| 5,614,283 | A | 3/1997 | Potnis et al. | |
| 6,420,626 | B1 * | 7/2002 | Erspamer et al. | 604/378 |
| 6,790,798 | B1 | 9/2004 | Suzuki et al. | |
| 8,263,820 | B2 * | 9/2012 | Carlucci et al. | 604/370 |
| 2003/0208175 | A1 * | 11/2003 | Gross et al. | 604/378 |
| 2006/0206073 | A1 | 9/2006 | Crane et al. | |

FOREIGN PATENT DOCUMENTS

| EP | 0 875 224 A1 | 11/1998 |
| EP | 0 724 418 B1 | 3/1999 |
| EP | 1 447 067 B1 | 2/2003 |
| EP | 0 826 349 B1 | 11/2006 |

OTHER PUBLICATIONS

PCT International Search Report dated Jan. 23, 2009, 10 pages.

\* cited by examiner

*Primary Examiner* — Lynne Anderson
*Assistant Examiner* — Kathryn E Ditmer
(74) *Attorney, Agent, or Firm* — Andres E. Velarde (57) ABSTRACT

Absorbent core for disposable absorbent articles, particularly for the absorption of menses or blood.

19 Claims, 3 Drawing Sheets

THIN ABSORBENT CORE SUBSTANTIALLY FREE OF CELLULOSE FIBERS

CROSS REFERENCE TO RELATED APPLICATION

This application is a continuation application of prior U.S. application Ser. No. 12/180,751 filed Jul. 28, 2008 now U.S. Pat. No. 8,263,820.

FIELD OF THE INVENTION

The present invention relates to an absorbent core for absorbent articles, for example sanitary napkins and the like.

BACKGROUND OF THE INVENTION

Absorbent articles for absorption of body fluids such as menses or blood are well known in the art, and comprise for example feminine hygiene articles such as sanitary napkins, panty liners, tampons, interlabial devices, as well as wound dressings, and the like. When considering for example sanitary napkins, these articles typically comprise a liquid-pervious topsheet as wearer-facing layer, a backsheet as garment-facing layer and an absorbent core between topsheet and backsheet. The body fluids are acquired through the topsheet and subsequently stored in the absorbent core. The backsheet typically prevents the absorbed fluids from wetting the wearer's garment.

An absorbent core can typically comprise one or more fibrous absorbent material, which in turn can comprise natural fibers, such as for example cellulose fibers, typically wood pulp fibers, synthetic fibers, or combinations thereof.

Absorbent articles can further comprise, typically in the absorbent core, superabsorbent materials, such as absorbent gelling materials (AGM), usually in finely dispersed form, e.g. typically in particulate form, in order to improve their absorption and retention characteristics. Superabsorbent materials for use in absorbent articles typically comprise water-insoluble, water-swellable, hydrogel-forming crosslinked absorbent polymers which are capable of absorbing large quantities of liquids and of retaining such absorbed liquids under moderate pressure. Absorbent gelling materials can be incorporated in absorbent articles, typically in the core structure, in different ways; for example, absorbent gelling materials in particulate form can be dispersed among the fibers of fibrous layers comprised in the core, or rather localized in a more concentrated arrangement between fibrous layers.

Absorbent cores for absorbent articles having a thin structure can further provide an improved immobilization of absorbent gelling materials, particularly when the article is fully or partially loaded with liquid, and an increased wearing comfort. Such thinner structures provide absorbent articles combining better comfort, discreetness and adaptability, such as for example, thin absorbent structures where the absorbent gelling material is located and somehow kept in selected, e.g. patterned regions of the structure itself.

EP 724418 (Tanzer) for example, discloses an absorbent article which includes superabsorbent material located in discrete pockets. The absorbent article comprises a first and a second carrier layer and water-sensitive attaching means for securing together the carrier layers and to provide a plurality of pocket regions. The article comprises high-absorbency material located within said pocket regions. The water-sensitive attachment means provides a wet strength which is less than a separating force imparted by a swelling of that high-absorbency material when that high-absorbency material is exposed to an aqueous liquid. The absorbent article is said to provide an absorbent structure which more securely locates and contains the high-absorbency material in said pockets when the article is dry. However, due to the construction of the pockets, it is believed that this absorbent article does not provide a very satisfactory immobilization of the absorbent material in the fully or partially urine loaded state.

EP 1447067, assigned to the Procter & Gamble Company, describes an absorbent article, typically a disposable absorbent article, such as a diaper, having an absorbent core which imparts increased wearing comfort to the article and makes it thin and dry. The absorbent core comprises a substrate layer, the substrate layer comprising a first surface and a second surface, the absorbent core further comprising a discontinuous layer of absorbent material, the absorbent material comprising an absorbent polymer material, the absorbent material optionally comprising an absorbent fibrous material which does not represent more than 20 weight percent of the total weight of the absorbent polymer material. The discontinuous layer of absorbent material comprises a first surface and a second surface, the absorbent core further comprising a layer of thermoplastic material, the layer of thermoplastic material comprising a first surface and a second surface and wherein the second surface of the discontinuous layer of absorbent material is in at least partial contact with the first surface of the substrate layer and wherein portions of the second surface of the layer of thermoplastic material are in direct contact with the first surface of the substrate layer and portions of the second surface of the layer of thermoplastic material are in direct contact with the first surface of the discontinuous layer of absorbent material.

While absorbent articles according to EP 1447067 and comprising thin absorbent cores with relatively high amounts of absorbent gelling materials and rather low content of fibrous materials commonly have good absorption and retention characteristics to body fluids like urine, there still remains room for improvement of absorption and retention towards other body fluids. In particular, menses and blood are particularly difficult to be effectively absorbed and retained into absorbent cores containing superabsorbent materials in major amounts since such materials do not show optimal absorption and retention characteristics towards such body fluids.

It is believed that the non-optimal absorption and retention are mainly caused by poor permeability of superabsorbent materials towards menses and blood due to the viscosity and/or to the complex nature of these fluids. Menses and blood are water based fluids comprising components having molecular weights higher than water and also corpuscular components, including red cells, white cells, soluble proteins, cellular debris and mucus, which slow down the absorption of these fluids by superabsorbents. Menses and blood are rather thick, and more difficult to absorb in conventional absorbent structures comprising absorbent gelling materials; moreover, corpuscular components like red cells may decrease the absorption capacity of certain superabsorbent particles. This translates into a slower initial uptake rate of the fluid into the superabsorbent material, and in turn in the absorbent structure comprising the superabsorbent material, which can result in a lower final absorption and retention capacity.

Also when considering more in general fibrous absorbent materials, different fibers and different fibrous structures may show different behaviors and effectiveness towards various body fluids, particularly towards menses and blood. For example, cellulose fibers, such as for example wood pulp fibers, show a greater absorption and diffusion capacity towards the water fraction of menses and blood, which may be very rapidly acquired and may be transported within the fibrous structure, far from the initial acquisition area, while the corpuscular and higher molecular weight components do not diffuse equally well, and may remain closer to the initial acquisition area. Such corpuscular and higher molecular weight components tend to travel preferentially in a direction perpendicular to the plane of the absorbent structure. Also, natural and synthetic fibrous materials can be more or less suitable to provide compact, or alternatively bulkier, absorbent structures to be employed in absorbent cores.

Hence, there is still the need for an improved, thin absorbent core structure for an absorbent article, particularly for absorption of menses or blood, which comprises the absorbent gelling material in a non uniform layer stably provided onto a substrate layer, and which takes advantage of the peculiarities of the different fibrous and non-fibrous absorbent materials in the absorption and management of these complex body fluids, achieving a better result in terms of fluid acquisition and distribution. Such a structure could also be stably thin, or in any case should not significantly change (for example increase) its thickness upon absorption throughout its normal use.

SUMMARY OF THE INVENTION

The present invention addresses the above need by providing an absorbent core for an absorbent article intended for absorption of menses or blood, comprising a substrate layer including a first surface and a second surface. The absorbent core further comprises a non uniform layer of absorbent material including an absorbent polymer material. The non uniform layer of absorbent material comprises a first surface and a second surface. The absorbent core further comprises a layer of a thermoplastic material including a first surface and a second surface, wherein the second surface of the non uniform layer of absorbent material is in at least partial contact with the first surface of the substrate layer. Portions of the second surface of the layer of thermoplastic material are in direct contact with the first surface of the substrate layer and portions of the second surface of the layer of thermoplastic material are in direct contact with the first surface of the non uniform layer of absorbent material. Further, the substrate layer comprises a fibrous material substantially free of cellulose fibers, and the substrate layer has a basis weight from 25 g/m$^2$ to 120 g/m$^2$, preferably from 35 g/m$^2$ to 90 g/m$^2$.

DETAILED DESCRIPTION OF THE INVENTION

Figure 1:
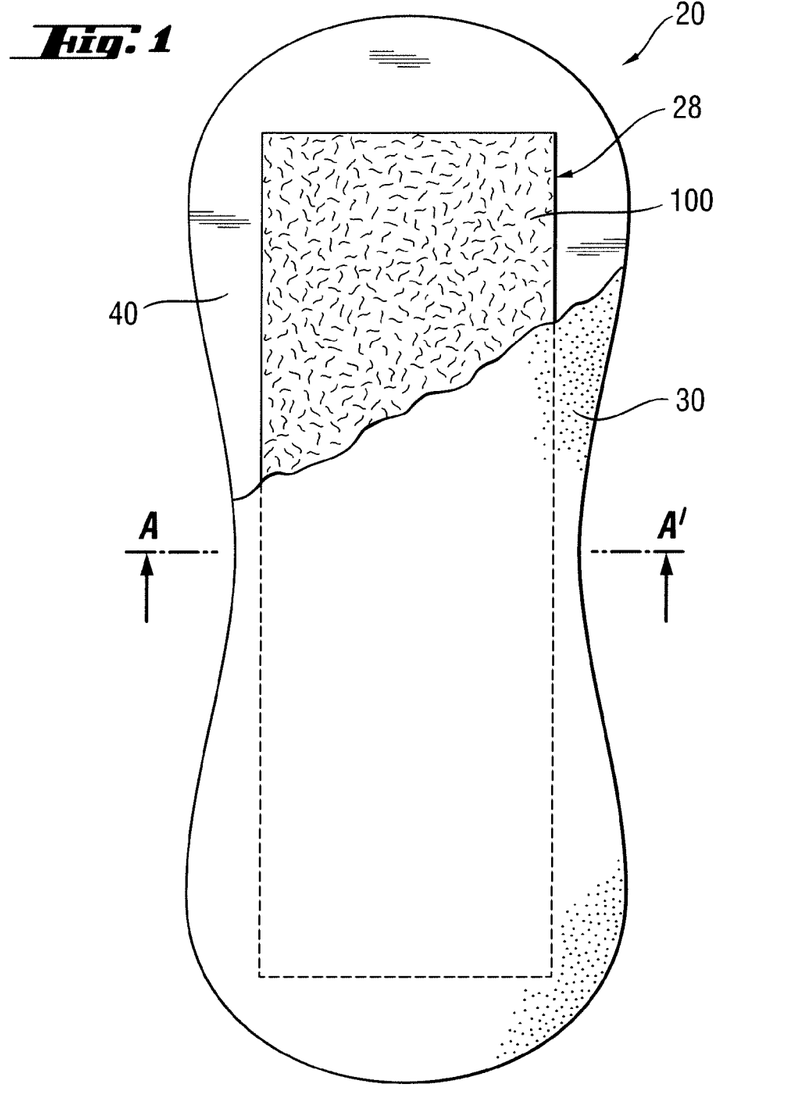
FIG. 1 is a plan view of a sanitary napkin showing an absorbent core according to an embodiment of the present invention.

The present invention relates to an absorbent core for absorbent articles such as sanitary napkins, panty liners, tampons, interlabial devices, wound dressings, and the like, which are intended for the absorption of body fluids, such as menses and blood. Exemplary absorbent articles in the context of the present invention are disposable absorbent articles. The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). The absorbent core of the present invention will be herein described in the context of a typical absorbent article, such as, for example, a sanitary napkin 20 as illustrated in FIG. 1. Typically, such articles as shown in FIG. 1 can comprise the elements of a liquid pervious topsheet 30, a backsheet 40 and an absorbent core 28 intermediate said topsheet 30 and said backsheet 40.

In the following description the term "cellulose fibers" is used. Cellulose fibers comprise naturally occurring fibers based on cellulose, such as, for example cotton, linen, etc. Wood pulp fibers are one example of cellulose fibers according to the present invention. Man-made fibers derived from cellulose, such as regenerated cellulose (rayon), or partially or fully acetylated cellulose derivatives (e.g. cellulose acetate or triacetate), are also considered as cellulose fibers according to the present invention.

In the following description of the invention, the surface of the article, or of each element thereof, which in use faces in the direction of the wearer is called wearer-facing surface. Conversely, the surface facing in use in the direction of the garment is called garment-facing surface. The absorbent article of the present invention, as well as any element thereof, such as, for example the absorbent core, has therefore a wearer-facing surface and a garment-facing surface.

Topsheet

According to the present invention, the absorbent article can comprise a liquid pervious topsheet. The topsheet suitable for use herein can comprise wovens, non-wovens, and/or three-dimensional webs of a liquid impermeable polymeric film comprising liquid permeable apertures. In FIG. 1 the topsheet is indicated with reference numeral 30. For example, the wearer-facing and contacting surface can be provided by a film material having apertures which are provided to facilitate liquid transport from the wearer facing surface towards the absorbent structure. Such liquid permeable, apertured films are well known in the art. They provide a resilient three-dimensional fiber-like structure. Such films have been disclosed in detail for example in U.S. Pat. Nos. 3,929,135, 4,151,240, 4,319,868, 4,324,426, 4,343,314, 4,591,523, 4,609,518, 4,629,643, 4,695,422 or WO 96/00548.

The topsheet for use herein can be a single layer or may have a multiplicity of layers. In an embodiment of the present invention, the topsheet across its full extension is a single layer, which provides both the wearer-facing surface and the garment-facing surface of the topsheet. Optionally, on the wearer-facing surface of the topsheet but only extending in the peripheral zone of the article an additional layer may be desirable to provide extra softness or extra liquid handling/retaining abilities (this design is usually referred to as "hybrid topsheet"). The topsheet typically extends across the whole of the absorbent structure and can extend into and form part of or all of the preferred but optional side flaps, side-wrapping elements, wings or ears. Also the topsheet can wrap around the absorbent core edges.

The topsheet as a whole shall be compliant, soft feeling, and non-irritating to the wearer's skin. It also can have elastic characteristics allowing it to be stretched in one or more directions. The topsheet may provide for acquisition and transport of fluid from the wearer towards the absorbent core and containment of the absorbent core. In addition to liquid permeability, the topsheet may have a high vapor permeability and/or air permeability.

Absorbent Core

In an embodiment of the present invention the absorbent core 28 comprises a substrate layer 100, absorbent polymer material 110 and a layer of thermoplastic material 120, typically a layer of fiberized hot melt adhesive 120. The substrate layer 100 is typically provided from a non-woven material, as will be explained in detail below.

The substrate layer 100 comprises a first surface and a second surface. At least portions of the first surface of the substrate layer 100 are in direct contact with a layer of absorbent polymer material 110. This layer of absorbent polymer material 110 can be typically a non uniform layer, and comprises a first surface and a second surface, wherein by "non uniform" it is meant that the absorbent polymer material 110 is distributed over the substrate layer 100 with non uniform basis weight. According to an embodiment of the present invention, the non uniform layer of absorbent polymer material 110 can be a discontinuous layer that is a layer typically comprising openings, i.e. areas substantially free of absorbent polymer material, which in certain embodiments can be typically completely surrounded by areas comprising absorbent polymer material, as will be explained in more detail later on. Typically these openings have a diameter or largest span of less than 10 mm, or less than 5 mm, or 3 mm, or 2 mm, or 1.5 mm and of more than 0.5 mm, or 1 mm. At least portions of the second surface of the absorbent polymer material layer 110 are in contact with at least portions of the first surface of the substrate layer material 100. The first surface of the absorbent polymer material 112 defines a certain height of the layer of absorbent polymer material above the first surface of the layer of substrate material 100. When the absorbent polymer material layer 110 is provided as a non uniform layer, typically for example as a discontinuous layer, at least some portions of the first surface of the substrate layer 100 are not covered by absorbent polymer material 110. The absorbent core 28 further comprises a layer of a thermoplastic material 120. This thermoplastic material 120 serves to at least partially immobilize the absorbent polymer material 110.

Figure 3:
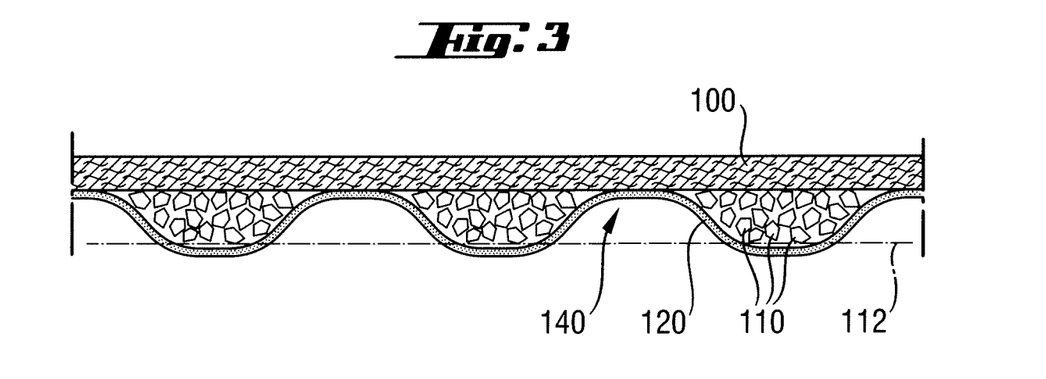
FIG. 3 shows a schematic cross section of an absorbent core according to one embodiment of the present invention.

In a typical embodiment of the present invention the thermoplastic material 120 is provided as a fibrous layer which is partially in contact with the absorbent polymer material 110 and partially in contact with the substrate layer 100. FIG. 3 shows such a structure. In this structure the absorbent polymer material layer 110 is provided as a discontinuous layer, a layer of fiberized thermoplastic material 120 is laid down onto the layer of absorbent polymeric material 110, such that the thermoplastic layer 120 is in direct contact with the first surface of the layer of absorbent polymer material 110, but also in direct contact with the first surface of the substrate layer 100, where the substrate layer is not covered by the absorbent polymeric material 110, i.e. in correspondence of the openings of the discontinuous layer of the polymer material 120. This imparts an essentially three-dimensional structure to the fibrous layer of thermoplastic material 120 which in itself is essentially a two-dimensional structure of relatively small thickness (in z-direction), as compared to the extension in x- and y-direction. In other words, the fibrous thermoplastic material layer 120 undulates between the first surface of the absorbent polymer material 110 and the first surface of the substrate layer 100. The areas where the fibrous thermoplastic material 120 is in contact with the substrate layer 100 are the areas of junction 140.

Thereby, the thermoplastic material 120 provides spaces to hold the absorbent polymer material 110 typically towards the substrate layer 100, and thereby immobilizes this material. In a further aspect, the thermoplastic material 120 bonds to the substrate 100 and thus affixes the absorbent polymer material 110 to the substrate 100. Typical thermoplastic materials will also penetrate into both the absorbent polymer material 110 and the substrate layer 100, thus providing for further immobilization and affixation.

Of course, while the thermoplastic materials disclosed herein can provide a much improved wet immobilization, i.e. immobilization of absorbent polymer material when the article is wet or at least partially loaded, these thermoplastic materials can also provide a very good immobilization of absorbent polymer material when the article is dry.

In accordance with an embodiment of the present invention, the absorbent polymer material 110 may also be optionally mixed with fibrous material, which can provide a matrix for further immobilization of the absorbent polymer material. However, typically a relatively low amount of fibrous material can be used, for example less than 40 weight %, less than 20 weight %, or less than 10 weight % of the total weight of the absorbent polymer material 110, positioned within the areas of absorbent polymer material.

Figure 5:
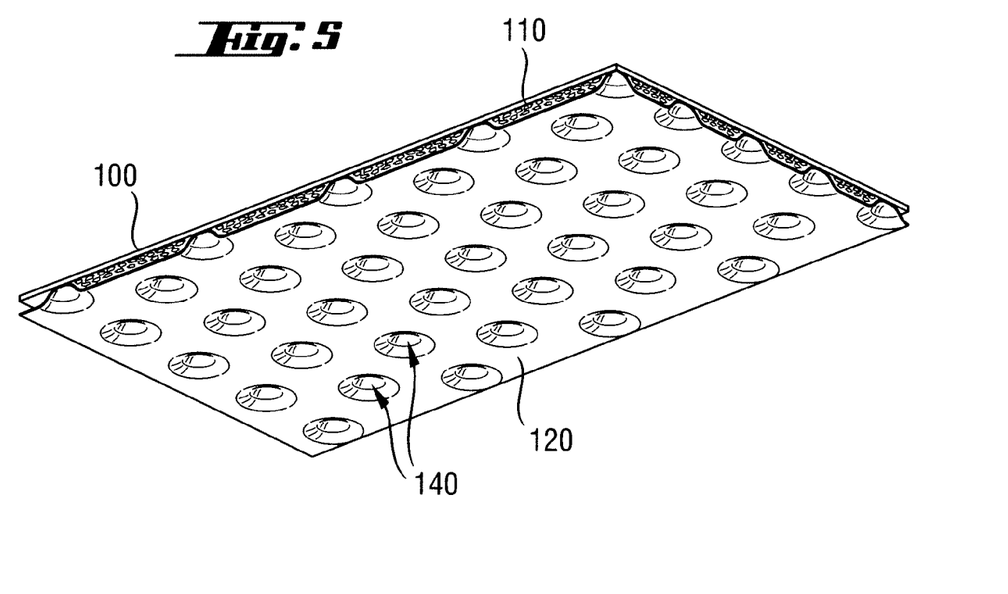
FIG. 5 shows a perspective view of an exemplary absorbent core according to the present invention.

According to an embodiment of the present invention, in a typically discontinuous layer of absorbent polymer material 110 the areas of absorbent polymer material can be connected to one another, while the areas of junction 140 can be areas, which in an embodiment may correspond to the openings in the discontinuous layer of absorbent polymer material, as shown for example in FIG. 5. The areas of absorbent material are then referred to as connected areas. In an alternative embodiment, the areas of junction 140 can be connected to one another. Then, the absorbent material can be deposited in a discrete pattern, or in other words the absorbent material represents islands in a sea of thermoplastic material 120. Hence, in summary, a discontinuous layer of absorbent polymer material 110 may comprise connected areas of absorbent polymer material 110, as e.g. illustrated in FIG. 5, or may alternatively comprise discrete areas of absorbent polymer material 110.

Figure 6:
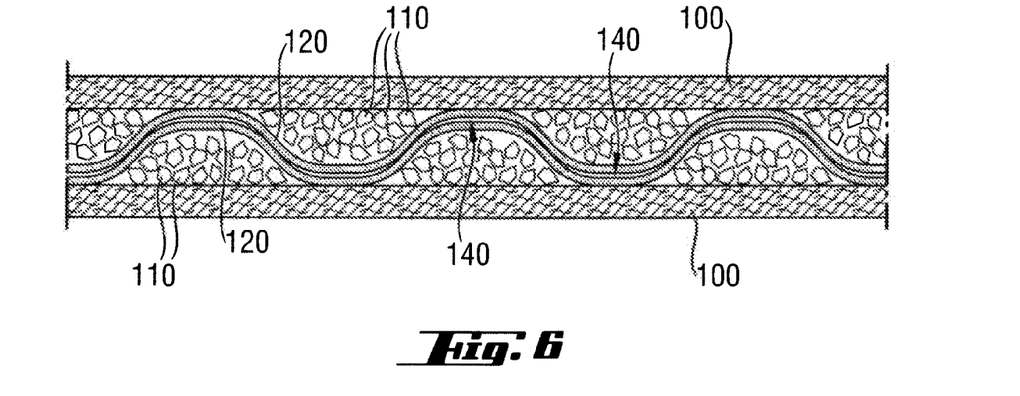
FIG. 6 shows a schematic cross section of an absorbent core according to one embodiment of the present invention.

In a further aspect of the present invention, it has been found that absorbent cores providing for a good wet immobilization can be formed by combining two layers as shown in FIG. 3 and as described in the context thereof. Such an embodiment is shown in FIG. 6. The absorbent core material shown in FIG. 6 comprises two substrate layers 100, two layers of absorbent polymer material 110 and two layers of fibrous thermoplastic material 120. When two e.g. discontinuous layers of an absorbent polymer material 110 are used, they would be typically arranged in such a way that the absorbent polymer material of the one layer faces the areas of junction 140 of the other layer, which in the two combined layers can be then offset without facing each other. Hence typically, when two storage layers are joined, this is done such that the first surface of the substrate layer 100 of the first storage layer faces the first surface of the substrate layer 100 of the second storage layer.

Figure 4:
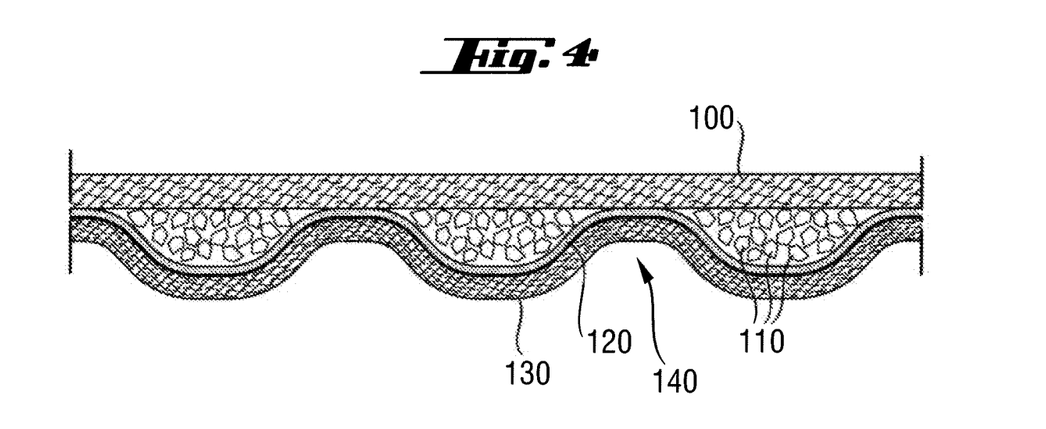
FIG. 4 shows a schematic cross section of an absorbent core according to one embodiment of the present invention.

An alternative embodiment of the present invention is shown in FIG. 4. The absorbent core shown in FIG. 4 can further comprise a cover layer 130. This cover layer may be provided of the same material as the substrate layer 100, or may be provided from a different material. Suitable materials for the cover layer are for example nonwoven materials, as will be better explained further on. In these embodiment portions of the cover layer 130 bond to portions of the substrate layer 100 via the thermoplastic material 120. Thereby, the substrate layer 100 together with the cover layer 130 provides spaces to immobilize the absorbent polymer material 110.

Figure 2:
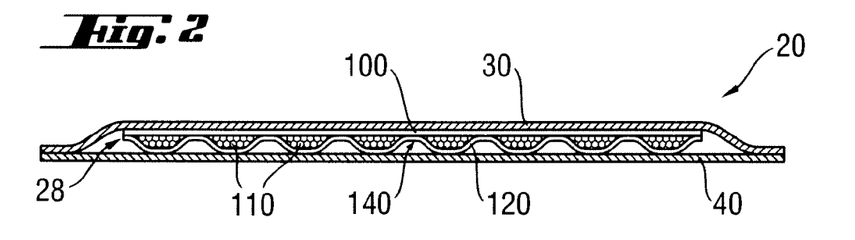
FIG. 2 is a schematic cross section of the sanitary napkin of FIG. 1 taken in the transverse axis A-A'.

The present invention, and specifically the embodiments described with reference to FIGS. 3, 4 and 6 can be used to provide a storage layer of an absorbent core. However, they can also be used to provide the full absorbent core 28 as illustrated in FIGS. 1 and 2. In that case, no further materials wrapping the core, such as a top layer and a bottom layer are being used. With reference to the embodiment of FIG. 3 the substrate layer 100 may provide the function of a top layer and the layer of fiberized thermoplastic material 120 may provide the function of a bottom layer of an absorbent core 28, wherein top and bottom layers respectively correspond to the body facing and garment facing surfaces of the core 28. With reference to FIG. 4 the cover layer 130 may provide the function of a bottom layer and the substrate layer 100 may provide the function of a top layer of an absorbent core. With reference to FIG. 6, the two substrate layers 100 used may provide the functions of a top layer and of a bottom layer of an absorbent core, respectively.

With reference to FIGS. 3 and 4 the areas of direct contact between the thermoplastic material 120 and the substrate material 100 are referred to as areas of junction 140. The shape, number and disposition of the areas of junction 140 will influence the immobilization of the absorbent polymer material 110. The areas of junction can be for example of squared, rectangular or circular shape. Areas of junction of circular shape can have a diameter of more than 0.5 mm, or more than 1 mm, and of less than 10 mm, or less than 5 mm, or less than 3 mm, or less than 2 mm, or less than 1.5 mm If the areas of junction 140 are not of circular shape, they can be of a size as to fit inside a circle of any of the diameters given above.

The areas of junction 140 can be disposed in a regular or irregular pattern. For example, the areas of junction 140 may be disposed along lines as shown in FIG. 5. These lines may be aligned with the longitudinal axis of the absorbent core, or alternatively they may have a certain angle in respect to the longitudinal edges of the core. A disposition along lines parallel with the longitudinal edges of the absorbent core 28 might create channels in the longitudinal direction which can lead to a lesser wet immobilization, hence for example the areas of junction 140 can be arranged along lines which form an angle of 20 degrees, or 30 degrees, or 40 degrees, or 45 degrees with the longitudinal edges of the absorbent core 28. Another pattern for the areas of junction 140 can be a pattern comprising polygons, for example pentagons and hexagons or a combination of pentagons and hexagons. Also typical can be irregular patterns of areas of junction 140, which also can give a good wet immobilization. Irregular patterns of areas of junction 140 can also give a better fluid handling behavior in case of absorption of menses or blood, since fluid can start diffusing in whichever direction from any initial acquisition point with substantially the same probability of contacting the absorbent polymer material in the e.g. discontinuous layer. Conversely, regular patterns might create preferential paths the fluid could follow with lesser probability of actually contacting the absorbent polymer material.

According to the present invention the thermoplastic layer 120 can comprise any thermoplastic material, typically adhesive thermoplastic materials, also referred to as hot melt adhesives. A variety of thermoplastic materials are suitable to immobilize the absorbent material. Some initially thermoplastic materials may later lose their thermoplasticity due to a curing step, e.g. initiated via heat, UV radiation, electron beam exposure or moisture or other means of curing, leading to the irreversible formation of a crosslinked network of covalent bonds. Those materials having lost their initial thermoplastic behavior are herein also understood as thermoplastic materials 120.

Without wishing to be bound by theory it has been found that those thermoplastic materials, i.e. the hot melt adhesives, can be most useful for immobilizing the absorbent polymer material 110, which combine good cohesion and good adhesion behavior. Good adhesion is critical to ensure that the thermoplastic layer 120 maintains good contact with the absorbent polymer material 110 and in particular with the substrate. Good adhesion is a challenge, namely when a non-woven substrate is used. Good cohesion ensures that the adhesive does not break, in particular in response to external forces, and namely in response to strain. The adhesive is subject to external forces when the absorbent product has acquired liquid, which is then stored in the absorbent polymer material 110 which in response swells. An exemplary adhesive should allow for such swelling, without breaking and without imparting too many compressive forces, which would restrain the absorbent polymer material 110 from swelling. It may be desirable that the adhesive not break, which would deteriorate the wet immobilization. Exemplary suitable thermoplastic materials are described below.

The thermoplastic material may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic composition may be a hot melt adhesive comprising at least one thermoplastic polymer in combination with other thermoplastic diluents such as tackifying resins, plasticizers and additives such as antioxidants.

The thermoplastic polymer can have typically a molecular weight (Mw) of more than 10,000 and a glass transition temperature (Tg) usually below room temperature. Typical concentrations of the polymer in a hot melt are in the range of 20-40% by weight. A wide variety of thermoplastic polymers can be suitable for use in the present invention. Such thermoplastic polymers can be typically water insensitive. Exemplary polymers can be (styrenic) block copolymers including A-B-A triblock structures, A-B diblock structures and (A-B)n radial block copolymer structures wherein the A blocks can be non-elastomeric polymer blocks, typically comprising polystyrene, and the B blocks can be unsaturated conjugated diene or (partly) hydrogenated versions of such. The B block can be typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable can be amorphous polyolefins or amorphous polyalphaolefins (APAO) which are homopolymers, copolymers or terpolymers of C2 to C8 alphaolefins.

The resin can typically have a Mw below 5,000 and a Tg usually above room temperature, typical concentrations of the resin in a hot melt can be in the range of 30-60%. The plasticizer has a low Mw of typically less than 1,000 and a Tg below room temperature, a typical concentration is 0-15%.

The thermoplastic material, typically a hotmelt adhesive, can be present in the form of fibers throughout the core, being provided with known means, i.e. the adhesive can be fiberized. Typically, the fibers can have an average thickness of 1-100 micrometer and an average length of 5 mm to 50 cm. In particular the layer of thermoplastic material, typically e.g. a hot melt adhesive, can be provided such as to comprise a net-like structure.

To improve the adhesiveness of the thermoplastic material 120 to the substrate layer 100 or to any other layer, in particular any other non-woven layer, such layers may be pre-treated with an auxiliary adhesive.

Typically, a hot melt adhesive can meet at least one or more of the following parameters. A typical hot melt adhesive can have a storage modulus G' measured at 20° C. of at least 30,000 Pa and less than 300,000 Pa, less than 200,000 Pa, or less than 100,000 Pa. The storage modulus G' at 20° C. is a measure for the permanent "tackiness" or permanent adhesion of the thermoplastic material used. Good adhesion will ensure a good and permanent contact between the thermoplastic material and for example the substrate layer 100. In a further aspect, the storage modulus G' measured at 60° C. should be less than 300,000 Pa and more than 18,000 Pa, or more than 24,000 Pa, or also more than 30,000. The storage modulus measured at 60° C. is a measure for the form stability of the thermoplastic material at elevated ambient temperatures. This value may be important if the absorbent product is used in a hot climate where the thermoplastic composition could lose its integrity if the storage modulus G' at 60° C. is not sufficiently high.

In a further aspect, the loss angle tan Delta of the adhesive at 60° C. should be below the value of 1, or below the value of 0.5. The loss angle tan Delta at 60° C. is correlated with the liquid character of an adhesive at elevated ambient temperatures. The lower tan Delta, the more an adhesive behaves like a solid rather than a liquid, i.e. the lower its tendency to flow or to migrate and the lower the tendency of an adhesive superstructure as described herein to deteriorate or even to collapse over time. This value is hence particularly important if the absorbent article is used in a hot climate.

In a further aspect, a typical hot melt adhesive should have a glass transition temperature Tg of less than 25° C., less than 22° C., less than 18° C., or less than 15° C. A low glass transition temperature Tg is generally beneficial for good adhesion. In a further aspect a low glass transition temperature Tg may help ensure that the adhesive thermoplastic material does not become too brittle.

In yet a further aspect, a typical hot melt adhesive can have a sufficiently high cross-over temperature Tx. The cross-over temperature parameter Tx is measured using the Dynamical Mechanical Analysis (DMA)—Temperature Sweep Test as referred to hereinafter. A sufficiently high cross-over temperature Tx has been found beneficial for high temperature stability of the thermoplastic material and hence it can ensure good performance of the absorbent product and in particular good wet immobilization even under conditions of hot climates and high temperatures. Therefore, Tx should typically be above 80° C., above 85° C., or above 90° C.

In a further aspect, hot melt adhesives in accordance with the present invention may have a sufficient cohesive strength parameter γ. The cohesive strength parameter γ is measured using the Rheological Creep Test as referred to hereinafter. A sufficiently low cohesive strength parameter γ is representative of elastic adhesive which, for example, can be stretched without tearing. If a stress of τ=1,000 Pa is applied, the cohesive strength parameter γ can be less than 100%, less than 90%, or less than 75%. For a stress of τ=125,000 Pa, the cohesive strength parameter γ can be less than 1,200%, less than 1,000%, or less than 800%.

An exemplary process for producing absorbent cores 28 in accordance with the present invention can comprise the following steps:

In one step, the substrate layer 100 is laid onto a formation surface. The absorbent polymeric material 110 is disposed by means known in the art, for example by means of a lay-down drum, in the selected non uniform e.g. discontinuous layer onto the substrate layer 100, optionally after providing a stabilizing adhesive on the substrate layer 100, for example in longitudinal stripes. In a further process step, a hot melt adhesive is placed with known means onto the absorbent polymer material, for example in form of fibers.

While any adhesive application means known in the art can be used to place the hot melt adhesive onto the absorbent polymer material, the hot melt adhesive can be typically applied by a nozzle system. For example, a nozzle system can be utilized, which can provide a relatively thin but wide curtain of adhesive. This curtain of adhesive is than placed onto the substrate layer 100 and the absorbent polymer material 110.

In an optional further process step, a cover layer 130 can be placed upon the substrate layer 100, the absorbent polymer material and the hot melt adhesive layer. The cover layer 130 will be in adhesive contact with the substrate layer 100 in the areas of junction 140. In these areas of junction 140 the adhesive is in direct contact with the substrate layer 100. The cover layer 130 will typically not be in direct adhesive contact with the substrate layer 100 where the absorbent polymer material 110 is present.

In one alternative embodiment, the cover layer 130 and the substrate layer 100 can be provided from a unitary sheet of material. The placing of the cover layer 130 onto the substrate layer 100 can then involve the folding of the unitary piece of material.

Hence, the uneven service of the lay-down system, which may be a lay-down drum, typically determines the distribution of absorbent polymer material in the non uniform, for example discontinuous layer and likewise can determine the pattern of areas of junction 140. The distribution of absorbent polymer material may be influenced by vacuum means.

The distribution of absorbent polymeric material can be profiled, for example profiled in the longitudinal direction, or in the lateral direction, or in both. Hence, for example, along the longitudinal axis of the absorbent core, which is normally coincident with the longitudinal axis of the absorbent article, for example a sanitary napkin, the basis weight of the absorbent polymer material can change. For example, the basis weight of absorbent polymer material in at least one freely selected first square measuring 1 cm×1 cm can be at least 10%, 20%, 30%, 40% or 50% higher than the basis weight of absorbent polymer material in at least one freely selected second square measuring 1 cm×1 cm. Typically the criterion is met if the first and the second square are centered about the longitudinal axis.

Typically the absorbent polymer material for absorbent cores according to the present invention can comprise absorbent polymer particles. Without wishing to be bound by theory it is believed that such material, even in the swollen state, i.e. when liquid has been absorbed, does not substantially obstruct the liquid flow throughout the material, particularly when further the permeability of said material, as expressed by the saline flow conductivity of the absorbent polymer material, is greater than 10, 20, 30 or 40 SFC-units, where 1 SFC unit is $1 \times 10^{-7}$ (cm$^3$×s)/g. Saline flow conductivity is a parameter well recognized in the art and is to be measured in accordance with the test disclosed in EP 752 892 B.

According to an embodiment of the present invention, the absorbent core can be provided as a single structure by known means. Thermo bonding or felting or combinations of these combining steps can for example create it. Hence, a core constituted by a single structure can be provided by laying the various materials described above onto each other in a continuous process, for example by air laying techniques, then a calendaring can take place in order to reduce the thickness and bulkiness of the structure as desired. The calendaring step can create a densification, which can provide the same force throughout the whole of the structure. This calendaring can be then optionally followed by thermo bonding or felting with needles or a combination such as felting with hot needles and a hot air exposure of the absorbent core structure, in order to attain a desired level of calliper, density and structure stabilization, which will in turn reflect on the final dimensional stabilization of the absorbent core.

The substrate layer 100 of the absorbent core 28 in FIGS. 2, 3, 4, and 6 can advantageously comprise a fibrous material substantially free of cellulose fibers. By saying that a layer of the absorbent core is "substantially free" of cellulose fibers, it is meant in the context of the present invention that the layer should not comprise any significant amount of cellulose fibers within its inner structure. While cellulose fibers which can be present at an outer surface of the specified layer, for example at the interface between the specified layer and an adjacent one, which could be for example an outer layer wrapping the core 28, in some cases can accidentally and slightly penetrate the structure of the specified layer, such shall not be considered significant. Significant amount can correspond to less than 10% by weight, less than 5% by weight, less than 3% by weight, or less than 1% by weight, based on the dry weight of the specified layer of the absorbent core. The substrate layer 100 can also have a basis weight from 25 $g/m^2$ to 120 $g/m^2$, or from 35 $g/m^2$ to 90 $g/m^2$.

In certain embodiments of the present invention the absorbent polymer material 110 in the absorbent core 28 is present throughout the area of the absorbent core in an average basis weight of less than 200 $g/m^2$, of less than 160 $g/m^2$, from 60 $g/m^2$ to 120 $g/m^2$, or from 80 $g/m^2$ to 100 $g/m^2$. An average basis weight is typically based on the whole area interested by the layer of absorbent polymer material, hence comprising possible openings included in an e.g. discontinuous layer.

Typical materials for the substrate layer 100 can be nonwoven materials, for example spunbonded or carded nonwoven materials, or also airlaid materials, such as for example latex and/or thermal bonded airlaid materials. Exemplary nonwoven materials can be provided from synthetic fibers, such as polyethylene (PE), polyethylene terephthalate (PET), polypropylene (PP). As the polymers used for nonwoven production are inherently hydrophobic, they can be typically coated with hydrophilic coatings, for example with durably hydrophilic coatings to provide permanently hydrophilic nonwovens. Other nonwoven materials can comprise composite structures such as a so called SMS material, comprising a spunbonded, a melt-blown and a further spunbonded layer.

In another embodiment of the present invention illustrated in FIG. 4, the absorbent core 28 can further comprise at least one cover layer 130 in direct contact with the first surface of the layer of thermoplastic material 120. According to an embodiment of the present invention, the cover layer 130 can comprise a same or similar fibrous material as that of the substrate layer 100, which hence can be substantially free of cellulose fibers and can e.g. have a basis weight from 25 $g/m^2$ to 120 $g/m^2$, or from 35 $g/m^2$ to 90 $g/m^2$.

Without being bound to any theory, it is believed that the absorbent core of the present invention has an improved capacity for the acquisition, management and retention of complex body fluids, particularly menses and blood, owing to the particular combination and composition of its material components and to the respective arrangement thereof, in addition to the already improved structure stability due to the better immobilization of the absorbent polymer material also when the article is fully of partially liquid loaded. The above advantages are achieved by a core structure which is particularly thin and flexible, and substantially shape stable, hence providing an absorbent article, typically a sanitary napkin, with an increased wearing comfort by being thin and dry.

In the absorbent core of the present invention, at least the fibrous substrate layer and the non uniform, e.g. discontinuous layer of absorbent material comprising the absorbent polymer material can each provide specific liquid absorption and management characteristics. Typically, as shown for example in FIG. 2, the absorbent core 28 can be positioned in the sanitary napkin 20 with the substrate layer 100 towards the wearer facing surface of the article. An absorbent core having the structure as shown in FIG. 6 is instead substantially symmetrical and can have in any case a substrate layer 100 towards the wearer facing surface of the article. In use the body fluid, typically menses or blood, can be hence directly received by a fibrous layer being substantially free of cellulose fibers, typically a substrate layer 100 as in the embodiment of FIG. 2. In the exemplary embodiment of FIGS. 1 and 2, the fluid can directly reach the fibrous substrate layer 100. The same occurs in the other embodiments where the absorbent core is as shown in FIG. 4 or 6, wherein the absorbent core of FIG. 4 can be typically positioned in an absorbent article with the substrate layer 100 towards the body facing surface of the article. In both cases the body fluid directly reaches a substrate layer 100 first.

The fibrous substrate layer being substantially free of cellulose fibers and having the selected basis weight and hence thickness typically comprises synthetic fibers which have a certain filtration capacity towards the corpuscular and complex fraction of menses or blood, typically red cells, white cells, soluble proteins, cellular debris and mucus. Upon receiving body fluid, said corpuscular and complex fraction of menses or blood is hence intercepted minimizing its direct interaction with the underlying absorbent polymer material, which could otherwise cause gel blocking. The complex body fluid is in fact at least partially "filtered" by the fibrous layer being free of cellulose fibers and having the selected basis weight, owing to the combined effect of its component synthetic fibers, and to its basis weight which in turn provides sufficient volume for an effective entrapment and immobilization of the corpuscular and complex components. In the exemplary embodiment of FIG. 2 the body fluid is directly acquired by the fibrous substrate layer 100, where the corpuscular part can be at least partially intercepted. The body fluid, typically menses or blood, is hence made less thick by this sort of filtration step, and can be subsequently released and more efficiently absorbed by the absorbent polymer material 120. In this exemplary embodiment the fluid can hence contact the absorbent polymer material after being previously "filtered" by the fibrous material substantially free of cellulose fibers and provided with the necessary volume in order to effectively entrap the corpuscular and complex fraction thereof. This substantially prevents complex components of menses or blood, particularly corpuscular components, from accumulating on the outer surface of the absorbent polymer material, for example superabsorbent particles, with a sort of shielding effect which causes gel blocking and makes further absorption problematic. The absorption capacity of the absorbent polymer material is instead directed more efficiently towards the water fraction of menses or blood.

This is achieved in a structure which is typically thin and is capable of employing more completely the absorption capacity of the different materials, which can hence be present in a typically lesser amount, thus also providing a particularly thin structure having improved dimensional stability during absorption and therefore increased comfort during use.

According to an embodiment of the present invention the absorbent polymer material can be selected among the polyacrylate based polymers described in the PCT Patent Application WO2007/047598, which are polyacrylate based materials very slightly crosslinked, or substantially not crosslinked at all, this further improving the above mentioned synergistic effect. Particularly, said polyacrylate based materials can have an extractable fraction of at least about 30% by weight, between 30% and 80% by weight, or between 32% and 70% by weight, evaluated according to the Extractables test method described in the above referenced application. Alternatively, said polyacrylate based materials can have a retention capacity of at least about 30 g/g, at least about 35 g/g, or at least about 40 g/g, evaluated according to the Centrifuge Retention Capacity test described in the above referenced application. Said polymers in fact are particularly effective in absorbing complex body fluids such as menses or blood, and upon absorption of such fluids do not generally show a marked swelling, followed by gel blocking, like traditional superabsorbents, but rather act to a certain extent as thickeners of the body fluid, immobilizing it as a sort of gelatinous mass within the absorbent structure, namely in the interstices among the fibers, without causing substantial swelling and in turn a sensible increase of the overall thickness of the absorbent core.

According to a further embodiment of the present invention, an absorbent article for absorption of body fluids such as menses or blood comprising an absorbent core 28, typically positioned such as to have the substrate layer 100 oriented towards the body facing surface of the article, can further comprise a fibrous acquisition layer between the absorbent core 28 and the topsheet, hence typically onto the body facing surface of the substrate layer 100. According to an embodiment of the present invention the acquisition layer can also comprise a fibrous material substantially free of cellulose fibers, namely for example nonwoven materials made by air laying or wet laying of synthetic fibers such as polyethylene (PE), polyethylene terephthalate (PET), or polypropylene (PP). Such a fluid acquisition layer substantially free of cellulose fibers would further improve the fluid acquisition and absorption mechanism as described above with reference to the intercepting/filtering capability of synthetic fibers towards the complex components of menses or blood.

Exemplary materials for the fluid acquisition layer could comprise spunbonded or carded nonwoven materials, or airlaid materials such as for example latex bonded or thermal bonded airlaid materials. Basis weights can typically range from $10 \text{ g/m}^2$ to $60 \text{ g/m}^2$, or from $25 \text{ g/m}^2$ to $40 \text{ g/m}^2$.

According to another embodiment of the present invention the absorbent article can comprise a further fibrous layer comprised between the absorbent core 28 and the backsheet, i.e. typically provided at the garment facing surface of the core. This optional layer can be provided by a fibrous material comprising cellulose fibers, typically not more than 60% by weight of cellulose fibers, or from 30% to 50% by weight of cellulose fibers. Examples of fibrous materials for this optional fibrous layer can be nonwoven materials, such as for example carded nonwovens, airlaid or wetlaid fibrous materials, such as for example latex or thermal bonded airlaid fibrous materials. Basis weights for this optional fibrous layer can typically range from $10 \text{ g/m}^2$ to $100 \text{ g/m}^2$, or from $40 \text{ g/m}^2$ to $80 \text{ g/m}^2$. This optional fibrous layer according to this further embodiment of the present invention can act as an added wicking layer receiving and distributing excess fluid which might not be fully retained by the absorbent core 28. Without being bound to any theory, the presence of cellulose fibers can make the layer particularly effective in acquiring and diffusing the water fraction of body fluids like menses or blood which is not completely absorbed by the absorbent polymer material of the absorbent core 28, moreover after at least a part of the complex fraction, particularly the corpuscular components, have been retained by the substrate layer 100 as explained above.

The further fibrous layer can be a separate layer, distinct from the core 28, and combined thereto in a known way while assembling the absorbent article, or can be part of the absorbent core, for example it can be provided by a suitably selected cover layer 130.

Backsheet

The absorbent article comprising the core according to the present invention can also comprise a backsheet 40. The backsheet primarily has to prevent the extrudes absorbed and contained in the absorbent structure from wetting materials that contact the absorbent article such as underpants, pants, pajamas, undergarments, and shirts or jackets, thereby acting as a barrier to fluid transport. The backsheet according to an embodiment of the present invention can also allow the transfer of at least water vapor, or both water vapor and air through it and thus allow the circulation of air into and water vapor out of the article. The backsheet can typically extend across the whole of the absorbent structure and can extend into and form part or all of side flaps, side wrapping elements or wings, if present.

The elements of the article may be joined by any means suitable for affixing two adjacent layers of material, such that the layers are directly attached to one another or directly attached to one another via the joining means. Suitable joining means include adhesive, fusion bonding, ultrasonic bonding, stitching, heat (e.g. thermo bonding by welding fibers at intersections or melting a polymer to attach fibers or films to each other), embossing, crimping, pressure bonds, dynamic mechanical bonds or combinations thereof.

Especially if the absorbent article finds utility as a sanitary napkin or panty liner, the absorbent article can be also provided with a panty fastening means, which provides means to attach the article to an undergarment. For example the panty fastening means may comprise a panty fastening adhesive on the garment facing surface of the backsheet, or alternatively a mechanical fastener such as hook and loop fasteners such as marketed under the trade name VELCRO, snaps or holders. The panty fastening adhesive provides a means for securing the article to the panty and optionally also a means for securing the article when soiled, to a fold and wrap package for convenient disposal.

The absorbent article comprising the absorbent core of the present invention can be used beneficially in the context of sanitary napkins. The absorbent article may thus also have all those features and parts, which are typical for products in the context of their intended use. For sanitary napkins this includes particularly wings or side flaps which are provided on the side edges of the napkin and which fold around the crotch edge of an undergarment. The side flaps can be provided as extensions of one or several of the elements of the napkin such as the topsheet and/or backsheet. They can also be made separately and be joined to the side margin of the napkin.

EXAMPLE

A sanitary napkin comprising an absorbent core according to an embodiment of the present invention is similar to that illustrated in FIGS. 1 and 2 and comprises a topsheet constituted by a polyethylene perforated formed film, a backsheet constituted by a 25 g/m² polyethylene film, a core comprising a substrate layer constituted by a 45 g/m² carded nonwoven comprising polyester fibers and PP/PE bicomponent fibers, available from BBA Fiberweb under the code TBPL 50/50 6 dpf philic PET/BICO, a discontinuous layer of absorbent polymer material constituted by a particulate superabsorbent material available from Nippon Shokubai under the trade name Aqualic L520 distributed onto the substrate layer in a non uniform layer having overall an average basis weight of 100 g/m², and a layer of thermoplastic material constituted by a hot melt adhesive available from HB Fuller under the trade name NV 1151 Zeropack applied in fibers having an average thickness of about 50 μm at a basis weight of 9 g/m².

The sanitary napkin further comprises a fibrous layer between the absorbent core and the backsheet, constituted by a 65 g/m² latex bonded airlaid (LBAL) material comprising 30% by weight cellulose fibers, 40% by weight PET fibers and 30% by weight latex binder, available from Concert GmbH under the code WHXX65.

The Rheological Creep Test and the Dynamical Mechanical Analysis (DMA)—Temperature Sweep Test mentioned hereinabove for measuring the cohesive strength parameter γ and the cross-over temperature parameter Tx respectively, are as described in the copending patent application EP 1447067, assigned to the Procter & Gamble Company.

Artificial Menstrual Fluid (AMF)

Artificial Menstrual Fluid is based on modified sheep's blood that has been modified to ensure it closely resembles human menstrual fluid in viscosity, electrical conductivity, surface tension and appearance. It is prepared as explained in U.S. Pat. No. 6,417,424, assigned to The Procter & Gamble Company, from line 33 of column 17 to line 45 of column 18, to which reference is made.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that is alone, or in any combination with any other reference or references, teaches, suggests or discloses any such invention. Further, to the extend that any meaning or definition of term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent core for an absorbent article intended for absorption of menses or blood, the core comprising a substrate layer;

the substrate layer comprising a substrate layer first surface and a substrate layer second surface;

the absorbent core further comprising a layer of absorbent material;

the absorbent material comprising an absorbent polymer material;

the layer of absorbent material comprising a layer of absorbent material first surface and a layer of absorbent material second surface;

the absorbent core further comprising a layer of a thermoplastic material; and the layer of thermoplastic material comprising a layer of thermoplastic material first surface and a layer of thermoplastic material second surface;

wherein the layer of absorbent material second surface is in at least partial contact with the substrate layer first surface, wherein portions of the layer of thermoplastic material second surface are in direct contact with the substrate layer first surface and portions of the layer of thermoplastic material second surface are in direct contact with the layer of absorbent material first surface, and wherein the substrate layer comprises a fibrous material substantially free of cellulose fibers, the substrate layer having a basis weight from about 25 g/m² to about 120 g/m²;

said absorbent article having in use a body facing surface and a garment facing surface, wherein said substrate layer in said absorbent core provides the function of a top layer to the absorbent core;

wherein the top layer of the absorbent core corresponds to the body facing surface of the core;

wherein said absorbent article further comprises a fibrous layer positioned below said core towards said garment facing surface of said absorbent article, wherein said fibrous layer comprises greater than zero and not more than 60% of cellulose fibres; and wherein the absorbent core comprises at least a cover layer in direct contact with the layer of thermoplastic material first surface.

2. An absorbent core according to claim 1, wherein the substrate layer has a basis weight from about 35 g/m² to about 90 g/m².

3. An absorbent core according to claim 1, wherein the layer of absorbent material is a discontinuous layer of absorbent material.

4. An absorbent core according to claim 1, wherein the absorbent polymer material is present throughout the area of the absorbent core in an average basis weight of greater than zero and less than about 200 g/m².

5. An absorbent core according to claim 1, wherein the absorbent polymer material is present throughout the area of the absorbent core in an average basis weight of greater than zero and less than about 160 g/m².

6. An absorbent core according to claim 1, wherein the absorbent polymer material is present throughout the area of the absorbent core in an average basis weight from about 60 g/m² to about 120 g/m².

7. An absorbent core according to claim 1, wherein the absorbent polymer material is present throughout the area of the absorbent core in an average basis weight from about 80 g/m² to about 100 g/m².

8. An absorbent core according to claim 1, wherein the thermoplastic material is a hot melt adhesive.

9. An absorbent core according to claim 1, wherein the thermoplastic material is fiberized.

10. An absorbent core according to claim 1, wherein the thermoplastic material comprises a net-like structure.

11. An absorbent article according to claim 1, wherein the fibrous layer comprises from about 30% to about 50% cellulose fibers.

12. A core according to claim 1, in an absorbent article, wherein the absorbent article further comprises a fluid acquisition layer positioned over the absorbent core towards the body facing surface, wherein the fluid acquisition layer is substantially free of cellulose fibers.

13. An absorbent core for an absorbent article intended for absorption of menses or blood, the core comprising a substrate layer;

the substrate layer comprising a substrate layer first surface and a substrate layer second surface;

the absorbent core further comprising a layer of absorbent material;

the absorbent material comprising an absorbent polymer material;

the layer of absorbent material comprising a layer of absorbent material first surface and a layer of absorbent material second surface;

the absorbent core further comprising a layer of a thermoplastic material; and the layer of thermoplastic material comprising a layer of thermoplastic material first surface and a layer of thermoplastic material second surface;

wherein the layer of absorbent material second surface is in at least partial contact with the substrate layer first surface, wherein portions of the layer of thermoplastic material second surface are in direct contact with the substrate layer first surface and portions of the layer of thermoplastic material second surface are in direct contact with the layer of absorbent material first surface, and wherein the substrate layer comprises a fibrous material substantially free of cellulose fibers, the substrate layer having a basis weight from about 25 g/m$^2$ to about 120 g/m$^2$;

said absorbent article having in use a body facing surface and a garment facing surface, wherein said substrate layer in said absorbent core provides the function of a top layer to the absorbent core;

wherein the top layer of the absorbent core corresponds to the body facing surface of the core;

wherein said absorbent article further comprises a fibrous layer positioned below said core towards said garment facing surface of said absorbent article, wherein said fibrous layer comprises greater than zero and not more than 60% of cellulose fibres; and wherein the absorbent core comprises at least a cover layer in direct contact with the layer of thermoplastic material first surface, and wherein the fibrous layer is provided by the cover layer of the absorbent core.

14. An absorbent article according to claim 13, wherein the fibrous layer comprises from about 30% to about 50% cellulose fibers.

15. An absorbent article according to claim 13, wherein the absorbent article further comprises a fluid acquisition layer positioned over the absorbent core towards the body facing surface, wherein the fluid acquisition layer is substantially free of cellulose fibers.

16. An absorbent core according to claim 13, wherein the absorbent polymer material is present throughout the area of the absorbent core in an average basis weight of greater than zero and less than about 200 g/m$^2$.

17. An absorbent core according to claim 13, wherein the layer of absorbent material is a discontinuous layer of absorbent material.

18. An absorbent core according to claim 13, wherein the thermoplastic material is a hot melt adhesive.

19. An absorbent core according to claim 13, wherein the thermoplastic material is fiberized.

\* \* \* \* \*